United States Patent [19]
Grant et al.

[11] Patent Number: 6,011,164
[45] Date of Patent: Jan. 4, 2000

[54] *BRASSICA NAPUS* VEGETABLE OIL WHEREIN THE LEVELS OF OLEIC, ALPHA-LINOLENIC, AND SATURATED FATTY ACIDS ARE ENDOGENOUSLY FORMED AND ARE SIMULTANEOUSLY PROVIDED IN AN ATYPICAL HIGHLY BENEFICIAL DISTRIBUTION VIA GENETIC CONTROL

[75] Inventors: Ian Grant; David G. Charne, both of Guelph, Canada

[73] Assignee: Pioneer Hi-Bred International, Inc., Johnston, Iowa

[21] Appl. No.: 09/207,574

[22] Filed: Dec. 8, 1998

Related U.S. Application Data

[60] Continuation of application No. 08/585,901, Jan. 16, 1996, Pat. No. 5,955,623, which is a division of application No. 08/399,926, Mar. 7, 1995, Pat. No. 5,625,130.

[51] Int. Cl.[7] .................................................... C07C 57/02
[52] U.S. Cl. ......................... 554/224; 554/223; 426/601; 426/615; 426/629
[58] Field of Search ................................... 554/223, 224; 424/601, 615, 629

[56] References Cited

U.S. PATENT DOCUMENTS

| | | |
|---|---|---|
| 4,277,412 | 7/1981 | Logan . |
| 4,297,292 | 10/1981 | Logan et al. . |
| 4,517,763 | 5/1985 | Beversdorf et al. . |
| 4,658,084 | 4/1987 | Beversdorf et al. . |
| 4,658,085 | 4/1987 | Beversdorf et al. . |
| 4,743,402 | 5/1988 | Fick . |

(List continued on next page.)

FOREIGN PATENT DOCUMENTS

| | | |
|---|---|---|
| 0 323 753 | 7/1989 | European Pat. Off. . |
| 323753 | 7/1989 | European Pat. Off. ......... A01H 1/02 |
| 0 647 406 | 4/1995 | European Pat. Off. . |
| WO 90/10380 | 9/1990 | WIPO . |
| WO 91/15578 | 10/1991 | WIPO . |
| WO 92/03919 | 3/1992 | WIPO . |

OTHER PUBLICATIONS

"The Development of Improved Rapeseed Cultivars", B.R. Stefansson from High and Low Erucic Acid Rapeseed Oils, Chapter 6, edited by John K.G. Kramer, Frank D. Sauer, and Wallace J. Pigden, pp. 143–159, Academic Press Canada (1983).

"The Introduction of Low Erucic Acid Rapeseed Varieties Into Canadian Production", J.K. Duan from High and Low Erucic Acid Rapeseed Oils, Chapter 6, edited by John K.G. Kramer, Frank D. Sauer, and Wallace J. Pigden, pp. 161–180, Academic Press Canada (1983).

(List continued on next page.)

*Primary Examiner*—Deborah D Carr
*Attorney, Agent, or Firm*—Burns, Doane, Swecker & Mathis, L.L.P.

[57] ABSTRACT

An improved Brassica oilseed, an improved plant capable of forming the same, and an improved edible endogenous vegetable oil derived from oilseed Brassica are provided. The edible endogenous vegetable oil of the present invention possesses an improved distribution of fatty acids following crushing and extraction in the absence of hydrogenation or other chemical or physical modification. The alpha-linolenic acid content is less than 3.5 percent by weight, the oleic acid content is at least 77 percent by weight, the total saturated fatty acid content is no more than 4.5 percent by weight, and the erucic acid content is no more than 2 percent by weight based upon the total fatty acid content. Each of the recited characteristics of the oil is controlled by genetic means and surprisingly is simultaneously expressed (e.g., in the field under conventional oilseed Brassica growing conditions) in the absence of cancellation as the result of the formation of the other recited traits. The improved Brassica oilseed is capable of forming upon germination a plant having satisfactory agronomic characteristics which yields following self-pollination Brassica oilseeds that possess the specified improved distribution of fatty acids within the oil that is present therein.

13 Claims, 1 Drawing Sheet

U.S. PATENT DOCUMENTS

| | | |
|---|---|---|
| 4,948,811 | 8/1990 | Spinner et al. . |
| 5,387,758 | 2/1995 | Wong et al. . |
| 5,434,283 | 7/1995 | Wong et al. ............ 554/224 |
| 5,545,821 | 8/1996 | Wong et al. . |

OTHER PUBLICATIONS

"Prospects for the Development of Rapeseed (B. napus L.) With Improved Linolenic and Linolenic Acid Content", by N.N. Roy and A.W. Tarr, *Plant Bleeding,* vol. 98, pp. 89–96 (1987).

"Genetic Control of Fatty Acid Composition in Oilseed Crops", R.K. Downey and D.G. Dorrell, *Proc. Flax Inst. U.S.A.,* vol. 47, No. 3, pp. 1–3 (1971).

*Changes and Limitations of Breeding for Improved Polyenoic Fatty Acids Content in Rapeseed,* Biotechnology for the Oils and Fats Industry, edited by Colin Ratledge, Peter Dawson, and James Rattray, American Oil Chemists'Society (1984).

*Genetical and Physiological Investigations on Mutants for Polyenoic Fatty Acids in Rapeseed, Brassica napus L.* by G. Róbbelen and A. Nitsch, Z. Pflanzenzúchtg., 75, pp. 93–105 (1975).

*Opportunities and Problems in Modification of Levels of Rapeseed $C^{18}$ Unsaturated Fatty Acids,* G. Rakow and D.I. McGregor, J. Am. Oil Chem. Soc., 50(10), pp. 400–403 (1973).

"Breeding for Improved C18–Fatty Acid Composition in Rapeseed (*Brassica napus L.*)", S. Pleines and W. Friedt, *Fat Sci. Technology,* 90(5), pp. 167–171 (1988).

"Breeding for Improved Fatty Acid Composition in Rapeseed", Roland Jónsson and Christer Persson, *Proc. 6th Int. Rapeseed Conference,* pp. 311–314 (1983).

Quality Breeding in Rapeseed—Svalóf 1886–1986 by Roland Jónsson and Bengt Uppstróm, pp. 173–183 (1986).

"Breeding of Improved Oil and Meal Quality in Rape (*Brassica napus L.*) and turnip rape (*Brassica campestris L.*)", Roland Jónsson, *Hereditas,* 87:205–218 (1977).

Kvalitetsfórádling av oljeváxter–resultat och mójligheter, Roland Jónsson, *Sveriges Utsadosforenings Tidskrift,* 94, pp. 36–38 (1984). (An English Translation also is provided.).

"Genotypes for High Oleic Acid Content (About 80%) in the Oil of Rapeseed (*Brassica napus L.*)", B.Y. Chen and B. Gertsson, *Crucif Newsletter,* 13, pp. 46–47 (1988).

Nuzpflanzen der Tropen und Subtropen, vol. IV, Pflanzenzúchtung, Armin Fuchs, S. Hirzel Verlag, Leipzig, pp. 155–177 (1980). (An English translation also is provided.).

Project Plan and Application for Contribution of Svalóf AB of Svalóv, Sweden, dated Feb. 25, 1986, by Dr. Roland Jonsson. (An English translation also is proviede.).

Project Plan and Application for Contribution of Svalóf AB of Svalóv, Sweden, dated Feb. 23, 1987 by Dr. Roland Jonsson. (An English translation also is provided.).

"Biotechnology for Brassica and Helianthus Improvement", Raghav Ram et al., Proceedings of the World Conference on Biotechnology for the Fats and Oils Industry (Sep. 27 –Oct. 2, 1987) from American Oil Chemists Society, pp. 65–71 (1988).

Proceedings of Sunflower Research Workshop, Feb. 1, 1984, Bismark, North Dakota, pp. 1,8–9.

BRASSICA NAPUS VEGETABLE OIL WHEREIN THE LEVELS OF OLEIC, ALPHA-LINOLENIC, AND SATURATED FATTY ACIDS ARE ENDOGENOUSLY FORMED AND ARE SIMULTANEOUSLY PROVIDED IN AN ATYPICAL HIGHLY BENEFICIAL DISTRIBUTION VIA GENETIC CONTROL

This application is a continuation of application Ser. No. 08/585,901, filed Jan. 16, 1996, now U.S. Pat. No. 5,955,623 which is a divisional of application Ser. No. 08/399,926, filed Mar. 7, 1995 (now U.S. Pat. No. 5,625,130).

BACKGROUND OF THE INVENTION

Oilseed Brassica is being grown as an increasingly important oilseed crop in many parts of the world. As a source of vegetable oil, it presently ranks behind only soybeans and palm and is virtually tied with sunflowers for the number three position of commercial importance. The oil is used as both a salad oil and a cooking oil throughout much of the world.

In its original form Brassica oil, often known as rapeseed oil, was found to have deleterious effects on human health due to its relatively high level of erucic acid which commonly is present in native cultivars in concentrations of 30 to 50 percent by weight based upon the total fatty acid content. In the past plant scientists identified a germplasm source of low erucic acid rapeseed oil. See, Chapter 6 entitled "The Development of Improved Rapeseed Cultivars" by B. R. Stefansson from "High and Low Erucic Acid Rapeseed Oils" edited by John K. G. Kramer, Frank D. Sauer, and Wallace J. Pigden, Academic Press Canada (1983).

In Canada, plant scientists focused their efforts on creating so-called "double-low" varieties which were low in erucic acid in the oil and low in glucosinolates in the solid meal remaining after oil extraction (i.e., an erucic acid content of less than 2 percent by weight based upon the total fatty acid content, and a glucosinolate content of less than 30 micromoles per gram of the oil-free meal). These higher quality forms of rape developed in Canada are known as canola.

In contrast, European scientists worked to achieve only "single-low" types which were low in erucic acid, but did not attempt to improve the quality of the solid meal which retained a glucosinolate content of about 100 micromoles per gram of oil-free meal. The result of this major change in the fatty acid composition of rapeseed oil was the creation of a new oil profile which often contained approximately 8 to 15 percent by weight of alpha-linolenic acid, approximately 62 percent by weight of oleic acid based upon the total fatty acid content, and approximately 6 percent or more by weight of saturated fatty acids in the form of stearic acid and palmitic acid based upon the total fatty acid content. Since the overall percentage of oil in the seed did not change appreciably when the new low erucic cultivars were developed, it appeared that the erucic acid oil component had been redirected into other fatty acids within the oil. See, Chapter 7 entitled "The Introduction of Low Erucic Acid Rapeseed Varieties Into Canadian Production" by J. K. Daun from the previously identified Academic Press Canada (1983) publication; "Prospects for the Development of Rapeseed (*B. napus L.*) With Improved Linoleic and Linolenic Acid Content" by N. N. Roy and A. W. Tarr, *Plant Breeding*, Vol. 98, Pages 89 to 96 (1987); and "Genetic Control of Fatty Acid Composition in Oilseed Crops" by R. K. Downey and D. G. Dorrell, *Proc. Flax Inst. U.S.A.*, Vol. 47, No. 3, Pages 1 to 3.

Over the years scientists have attempted to improve the fatty acids profile for canola oil. See, for instance, Chapter 10 by Gerhard Röbbelen entitled "Changes and Limitations of Breeding for Improved Polyenic Fatty Acids Content in Rapeseed" from "Biotechnology for the Oils and Fats Industry" edited by Colin Ratledge, Peter Dawson, and James Rattray, American Oil Chemists' Society (1984).

"Genetical and Physiological Investigations on Mutants for Polyenoic Fatty Acids in Rapeseed, *Brassica napus L.*" by G. Röbbelen and A. Nitsch appearing in *Z. Planzenzüchtg.*, 75, Pages 93 to 105 (1975), and "Opportunities and Problems in Modification of Levels of Rapeseed $C_{18}$ Unsaturated Fatty Acids" by G. Rakow and D. I. McGregor appearing in *J. Am. Oil Chem. Soc.* 50(10), Pages 400 to 403 (1973) are representative disclosures of a rapeseed mutant that includes a lesser than usual quantity of alpha-linolenic acid in the oil.

U.S. Pat. No. 4,948,811 discloses a salad/cooking oil wherein less desirable fatty acid components are physically separated from other fatty acid components following removal of the oil from rapeseeds. An operative straightforward means to provide the presently claimed highly advantageous distribution of fatty acids in the endogenous rapeseed oil was totally absent.

International Publication No. WO90/10380, published Sep. 20, 1990, and European Patent Application No. 0 343 753, entitled "Production of Improved Rapeseed Exhibiting an Enhanced Oleic Acid Content" published Jul. 12, 1989, disclose the production of rapeseeds that include a greater than usual concentration of oleic acid in the oil. A similar disclosure is found in commonly assigned U.S. patent application Ser. No. 286,708, filed Dec. 20, 1988. The presently claimed highly advantageous distribution of fatty acids was not disclosed.

International Publication No. WO91/15578, published Oct. 17, 1991, entitled "Production of Improved Rapeseed Exhibiting a Reduced Saturated Fatty Acid Content" discloses the production of a rapeseed that includes a lesser than usual concentration of stearic and palmitic acids in the oil. A similar disclosure is found in U.S. Pat. Nos. 5,387,758, 5,434,283 and 5,545,821. The presently claimed highly advantageous distribution of fatty acids was not disclosed.

International Publication No. WO92/03919 published Mar. 19, 1992, entitled "Seeds, Plants and Oils With Altered Fatty Acids Profiles" discloses an effort to modify the fatty acid distribution in an oil obtained from rapeseeds. The presently claimed highly advantageous distribution of fatty acids was not disclosed.

As reported in U.S. Pat. Nos. 4,517,763; 4,658,084; and 4,658,085; hybridization processes suitable for the production of rapeseed are known wherein herbicide tolerance is utilized.

The need has remained for an edible endogenous vegetable oil obtained from Brassica seeds in the absence of hydrogenation or other chemical or physical modification that possesses an improved overall distribution alpha-linolenic acid in a low concentration, oleic acid in a high concentration, saturated fatty acids in an extremely low concentration, and erucic acid in a low concentration simultaneously as claimed herein. In view of the highly complex nature of the molecular elongation and desaturation pathways that are operative during fatty acid formation in Brassica oilseeds, the achievement of this goal has not been realized by skilled researchers in the past as evidenced by the data reported in the above-identified publications.

It is an object of the present invention to provide an improved mature Brassica oilseed capable of yielding an edible endogenous vegetable oil having a novel improved distribution of fatty acids following simple crushing and extraction.

It is an object of the present invention to provide an oilseed Brassica plant having satisfactory agronomic characteristics which upon self-pollination is capable of forming Brassica oilseeds that yield an endogenous vegetable oil having a novel improved distribution of fatty acids following simple crushing and extraction.

It is another object of the present invention to provide an improved edible vegetable oil having a novel improved distribution of fatty acids formed by the simple crushing and extraction of Brassica oilseeds in the absence of hydrogenation or other chemical or physical modification.

It is a further object of the present invention to provide an improved endogenous vegetable oil derived from Brassica oilseeds in the absence of hydrogenation or other chemical or physical modification of good flavor having improved health and nutritional characteristics combined with attractive stability characteristics that is produced on a highly economical basis.

It is another object of the present invention to provide mature Brassica oilseeds capable of yielding an edible endogenous oil having an improved distribution of fatty acids that renders it suitable for a number of different end uses thereby simplifying the handling, crushing and refining requirements for such seed product.

It is yet another object of the present invention to provide on an expeditious and economically feasible basis a novel endogenous oil derived from Brassica oilseeds that is well suited for a wide range of end uses thereby simplifying storage and inventory considerations for those who supply the improved vegetable oil of the present invention.

These and other objects and advantages of the invention will be apparent to those skilled in the art from a reading of the following description and appended claims.

SUMMARY OF THE INVENTION

A mature Brassica oilseed is provided that is capable of yielding an edible endogenous vegetable oil having an improved distribution of fatty acids, the Brassica oilseed bearing an oil which exhibits following crushing and extraction in the absence of hydrogenation or other chemical or physical modification (1) an alpha-linolenic acid content of less than 3.5 percent by weight based upon the total fatty acid content, (2) an oleic acid content of at least 77 percent by weight based upon the total fatty acid content, (3) a total saturated fatty acid content of no more than 4.5 percent by weight based upon the total fatty acid content, and (4) an erucic acid content of no more than 2 percent by weight based upon the total fatty acid content, and wherein each of the recited traits of the oil is controlled by genetic means in the absence of cancellation as the result of the formation of the other recited traits, and wherein the Brassica oilseed is capable of forming upon germination an oilseed Brassica plant having satisfactory agronomic characteristics which yields following self-pollination Brassica oilseeds that possess the specified improved distribution of fatty acids within the oil present therein.

An oilseed Brassica plant is provided having satisfactory agronomic characteristics which upon self-pollination is capable of forming oilseeds that yield an endogenous vegetable oil having an improved distribution of fatty acids, the oilseeds bearing an oil which exhibits following crushing and extraction in the absence of hydrogenation or other chemical or physical modification (1) an alpha-linolenic acid content of less than 3.5 percent by weight based upon the total fatty acid content, (2) an oleic acid content of at least 77 percent by weight based upon the total fatty acid content, (3) a total saturated fatty acid content of no more than 4.5 percent by weight based upon the total fatty acid content, and (4) an erucic acid content of no more than 2 percent by weight based upon the total fatty acid content, and wherein each of the recited traits of the oil is controlled by genetic means in the absence of cancellation as the result of the formation of the other recited traits.

An improved edible endogenous vegetable oil is provided having an improved distribution of fatty acids formed by the crushing and extraction of Brassica oilseeds in the absence of hydrogenation or other chemical or physical modification which exhibits (1) an alpha-linolenic acid content of less than 3.5 percent by weight based upon the total fatty acid content, (2) an oleic acid content of at least 77 percent by weight based upon the total fatty acid content, (3) a total saturated fatty acid content of no more than 4.5 percent by weight based upon the total fatty acid content, and (4) an erucic acid content of no more than 2 percent by weight based upon the total fatty acid content, and wherein each of the recited traits of the oil was controlled by genetic means in the absence of cancellation as the result of the formation of the other recited traits.

DESCRIPTION OF PREFERRED EMBODIMENTS

Figure 1:
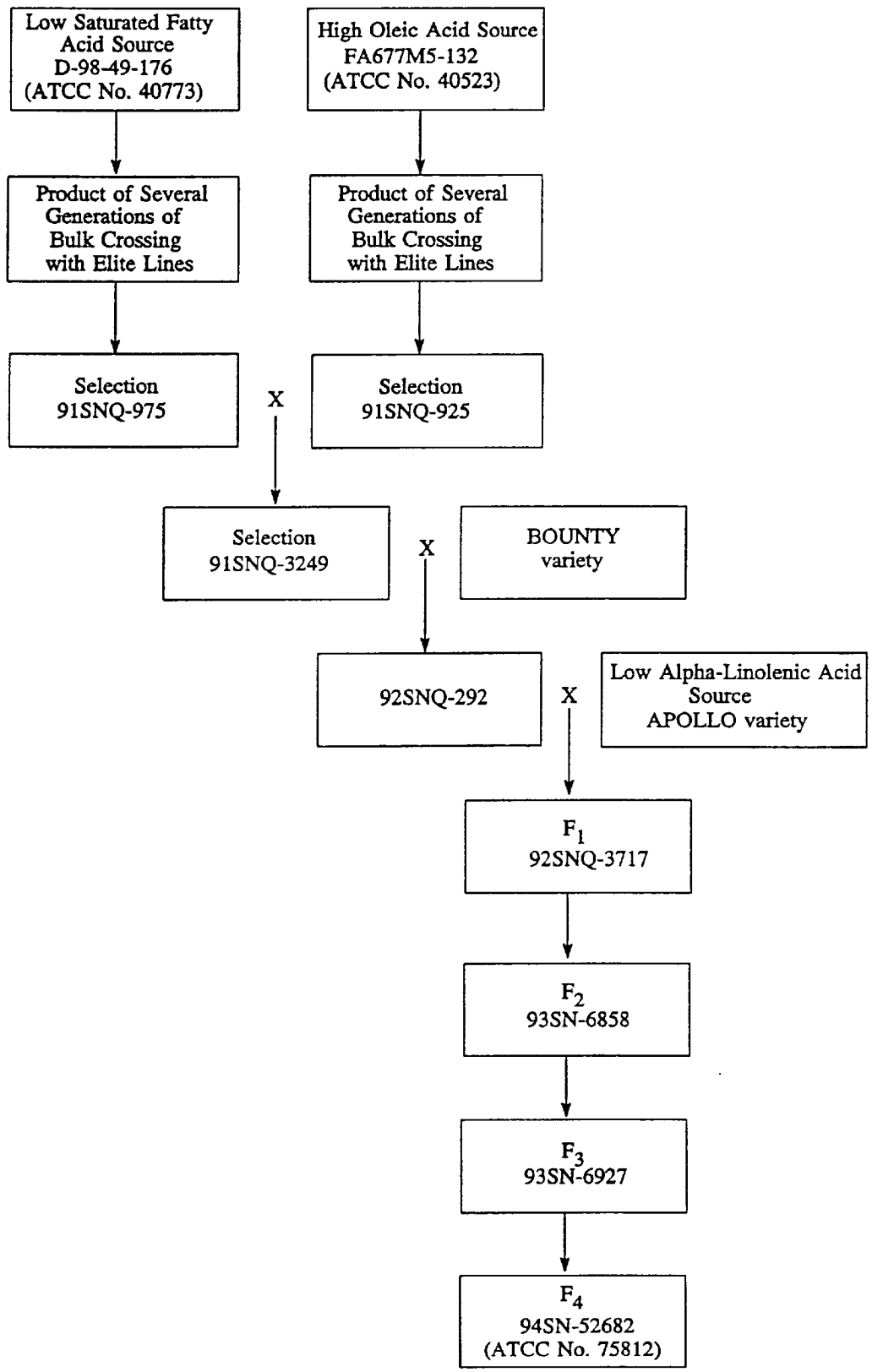
FIG. 1 illustrates by way of exemplification the formation of new *Brassica napus* plant material in accordance with the present invention designated 94SN-52682 as described in greater detail in Example I.

The fatty acid concentrations discussed herein are determined in accordance with a standard procedure wherein the oil is removed from the Brassica oilseeds by crushing and is extracted as fatty acid methyl esters following reaction with methanol and sodium methoxide. Next the resulting ester is analyzed for fatty acid content by gas liquid chromatography using a capillary column which allows separation on the basis of the degree of unsaturation and chain length. This analysis procedure is described in the work of J. K. Daun et al, *J. Amer. Oil Chem. Soc.*, 60: 1751–1754 (1983) which is herein incorporated by reference.

A novel edible endogenous vegetable oil is obtained from Brassica oilseeds in the absence of hydrogenation or other chemical or physical modification that possesses an improved overall distribution of alpha-linolenic acid in a low concentration, oleic acid in a high concentration, saturated fatty acids in an extremely low concentration, and erucic acid in a low concentration as specified hereafter. Each trait is controlled by genetic means and is surprisingly expressed in a novel combination in the absence of cancellation as the result of the formation of other recited traits. The low concentration of alpha-linolenic acid as specified imparts increased oxidative stability. The high concentration of oleic acid as specified further imparts increased thermal and oxidative stability and additionally provides nutritional benefits. The extremely low concentration of saturated fatty acids as specified imparts a significant nutritional benefit for those concerned with the minimization of serum cholesterol. Also, the low concentration of erucic acid as specified offers a nutritional benefit. The novel edible endogenous oil of the present invention is formed by the simple crushing of the Brassica oilseeds and the simple physical extraction of the oil without the expense of hydrogenation or other chemical or physical modification.

It unexpectedly has been found through empirical research that each of the recited traits of the endogenous vegetable oil of the present invention can be provided while under the control of independent genetic means, and can be combined by plant breeding (e.g., by pyramiding) or other suitable means, and subsequently expressed in a resulting rape plant without cancellation by one or more of the other of the recited traits. The required genetic means for each trait can be formed by the mutagenesis of available conventional oilseed Brassica germplasm, or can be selected from available non-conventional sources of oilseed Brassica germplasm which may already include naturally occurring or induced mutations capable of expressing one or more of the recited traits. During the combination a plant having one or two of the required genetic means for a specified trait or traits can serve as either a male or female parent.

When carrying out mutagenesis, one preferably selects plant cells capable of regeneration (e.g., seeds, microspores, ovules, pollen, vegetative parts) from any of the oilseed Brassica varieties (e.g., canola) which are recognized to have superior agronomic characteristics. Such plant cells may be derived from *Brassica napus, Brassica campestris*, or *Brassica juncea* plants. The *Brassica napus* plants may be of either the summer or winter types. The oilseed Brassica plant cells are subjected in at least one generation to mutagenesis, and an oilseed Brassica plant is regenerated from the cells to produce an oilseed Brassica plant and to form a Brassica oilseed in at least one subsequent generation that possesses the ability to form one or more of the atypical fatty acid oil quality traits as specified in detail hereafter with each trait being under genetic control. Parent oilseed Brassica plants possessing the requisite genetic means for the expression of a specified fatty acid trait may be produced following mutagenesis via self-pollination for a sufficient number of generations (e.g., 2 to 8 generations) to achieve substantial genetic homogeneity. Alternatively, the desired characteristic may be fixed through the formation of a new plant from a haploid microspore cell, causing the haploid to double, and producing a homozygous diploid plant in accordance with known techniques.

The mutagenesis preferably is accomplished by subjecting the plant cells (e.g., an oilseed) to a technique selected from the group consisting of contact with a chemical mutagen, gamma irradiation, and a combination of the foregoing, for a sufficient duration to accomplish the desired genetic modification but insufficient to completely destroy the viability of the cells and their ability to be regenerated into a plant. The Brassica oilseed preferably possesses a moisture content of approximately 5 to 6 percent by weight at the time of such metagenesis. The desired mutagenesis may be accomplished by use of chemical means, such as by contact with ethylmethylsulfonate, ethylnitrosourea, etc., and by the use of physical means, such as x-rays, etc. The mutagenesis also may be carried out by gamma radiation, such as that supplied by a Cesium 137 source. The gamma radiation preferably is supplied to the plant cells (e.g., an oilseed) in a dosage of approximately 60 to 200 Krad., and most preferably in a dosage of approximately 60 to 90 Krad. It should be understood that even when operating at radiation dosages within the ranges specified, some plant cells (e.g., oilseeds) may completely lose their viability and must be discarded. See commonly assigned U.S. patent application Ser. No. 286,708, filed Dec. 20, 1988, for a further discussion of the genetically controlled oleic acid trait and its formation, and commonly assigned U.S. Pat. No. 5,387,758 for a further discussion of the genetically controlled saturated fatty acid and trait and its formation. The contents of these disclosures are herein incorporated by reference.

It will be appreciated that the mutagenesis treatment potentially will result in a wide variety of genetic changes within the oilseed Brassica plants which are produced. Many of these changes will be deleterious to the viability of the resulting plant over an extended period of time. Some changes also will produce viable plants which possess deficient agronomic characteristics. Such off-types may be simply discarded. Alternatively, plants which have undergone the desired mutation production coupled with undesirable agronomic traits can be retained and used as breeding or source material from which plants having the targeted traits coupled with satisfactory agronomic characteristics ultimately are derived by plant breeding.

Following mutagenesis, oilseed Brassica plants are regenerated from the treated cells using known techniques. For instance, the resulting oilseeds may be planted in accordance with conventional Brassica-growing procedures and following self-pollination Brassica oilseeds are formed thereon. Alternatively, doubled haploid plantlets may be extracted to immediately form homogeneous plants. The planting of the treated Brassica oilseed preferably is carried out in a greenhouse in which the pollination is carefully controlled and monitored. Additional Brassica oilseeds which are formed as a result of such self-pollination in the present or a subsequent generation are harvested and are subjected to analysis for the desired trait. Since *Brassica napus, Brassica campestris,* and *Brassica juncea* are dicotyledons, the analysis for a desired mutation can be carried out on a single cotyledon (i.e., halfseed), and the remaining halfseed can be retained for possible future germination if the desired mutation is found following the mutagenesis. The oilseeds can be carefully separated into two halfseeds prior to such analysis using known techniques.

When a mature halfseed is found to possess a desired mutation, the other halfseed, which will be genetically the same as the halfseed which was subjected to halfseed analysis, can next be caused to germinate and an oilseed Brassica plant is formed from the same and is allowed to undergo self-pollination. Such planting of the halfseed preferably also is carried out in a greenhouse in which the pollination is carefully controlled and monitored. The resulting oilseeds formed on a plant resulting from the halfseed are harvested, planted, and are self-pollinated for a sufficient number of generations to achieve substantial genetic homogeneity. The genetic stabilization of the oilseed Brassica plant material enables the creation of plants having a reasonably predictable genotype which can be used as breeding or source material.

In accordance with the concept of the present invention it is essential that the edible endogenous vegetable oil of the Brassica oilseed contain an alpha-linolenic acid content of less than 3.5 (e.g., 1 to less than 3.5) percent by weight based upon the total fatty acid content that is controlled by genetic means in combination with the other recited components as specified. Oilseed Brassica germplasm containing the requisite genetic determinant for this alpha-linolenic acid trait is known and is publicly available. For instance, rape germplasm for this trait has been available in Germany from the mid-1970's, and in North American since 1983. Representative commercially available rape varieties that include the genetic means for the expression of this low alpha-linolenic acid trait include STELLAR, and APOLLO. A particularly preferred source for the requisite genetic means for the expression of alpha-linolenic acid in the stated concentration is the APOLLO variety that was developed at the University of Manitoba, and was registered in Canada as No. 3,694 during February, 1992, following the receipt of support from the Western Canadian Canola and Rapeseed Recommending Committee.

Seed for the production of the APOLLO spring canola *Brassica napus* variety is available from the University of Manitoba, Winnipeg, Manitoba, Canada. The yield of the APOLLO variety commonly exceeds that of the STELLAR variety which was the first low alpha-linolenic acid rapeseed variety registered in Canada. Also, genetic means for the expression of such trait can be obtained from 94SN-53574 (ATCC Assession No. 75813), 94SN-53662 (ATCC Assession No. 75814), and 94SN-52682 (ATCC Assession No. 75812) discussed hereafter. Such low concentration of alpha-linolenic acid in the oilseed Brassica oil serves to impart increased oxidative stability to the oil thereby making possible an extended shelf life.

The edible endogenous vegetable oil of the Brassica oilseeds contains oleic acid in a concentration of at least 77 (e.g., at least 77 up to approximately 84) percent by weight based upon the total fatty acid content that is controlled by genetic means in combination with the other recited components as specified. In a preferred embodiment the oleic acid component is provided in a concentration of at least 80 percent up to approximately 84 percent by weight based upon the total fatty acid content. The formation of the genetic means for the expression of such oleic acid trait is further described in WO90/10380 that is herein incorporated by reference. Genetic means for the expression of such trait can be obtained from FA677-39 (ATCC Assession No. 40409), FA677M5-132 (ATCC Assession No. 40523), and Topas H6-90 (ATCC Assession No. 40524). Also, genetic means for the expression of such trait can be obtained from 94SN-53574 (ATCC Assession No. 75813), 94SN-53662 (ATCC Assession No. 75814), and 94SN-52682 (ATCC Assession No. 75812) discussed hereafter. Care should be taken to select a high oleic acid mutant in which there has been no significant modification of non-seed lipid production that would otherwise interfere with the ultimate achievement of satisfactory agronomic characteristics. Such high concentration of oleic acid provides significant fatty acid mono-unsaturation in the rapeseed oil and supplies a health and nutritional benefit. Also, an increased thermal and oxidative stability is provided when compared to fatty acid components that possess a greater level of unsaturation.

Included in the endogenous vegetable oil of the Brassica oilseeds according to the present invention is an extremely low total saturated fatty acid content of no more than 4.5 (e.g., 2.5 to 4.5) percent by weight based upon the total fatty and content that is controlled by genetic means in combination with the other recited components as specified. Such total fatty acid content commonly consists primarily of palmitic acid containing 16 carbon atoms per molecule and stearic acid containing 18 carbon atoms per molecule. Lower saturated fatty acids, such as lauric acid containing 12 carbon atoms per molecule and myristic acid containing 14 carbon atoms per molecule, commonly are not present or are present in only trace amounts. Higher saturated fatty acids, such as arachidic acid containing 20 carbon atoms per molecule, behenic acid containing 22 carbon atoms per molecule, and lignoceric acid containing 24 carbon atoms per molecule, commonly are present in the resulting Brassica oil in extremely low and/or non-detectable concentrations and are less of a concern from a health and nutritional standpoint since they are not readily digestible by humans and therefore are not believed to contribute to serum cholesterol levels as do the saturated fatty acids having shorter molecular chain lengths. The endogenous vegetable oil of the Brassica oilseeds of the present invention preferably possesses a saturated fatty acid content of approximately 2 to 4 (e.g., approximately 2 to 3.5 or 2.5 to 3.5) percent by weight based upon the sum of stearic and palmitic acids in relation to the total fatty acid content. The formation of the genetic means for the expression of the saturated fatty acid content is further described in WO91/15578 and U.S. Pat. No. 5,387,758 that are herein incorporated by reference. Genetic means for the expression of such trait can be obtained from F32-38-172-X (ATCC Assession No. 40624) and D-98-49-176 (ATCC Assession No. 40773). Also, genetic means for the expression of such trait can be obtained from 94SN-53574 (ATCC Assession No. 75813), 94SN-53662 (ATCC Assession No. 75814), and 94SN-52682 (ATCC Assession No. 75812) discussed hereafter. Such extremely low concentration of saturated fatty acids offers a significant nutritional and health benefit to the consumer that is expected to make possible a reduced serum cholesterol level and accompanying health benefits to persons seeking to control serum cholesterol levels via diet.

Erucic acid is included in the endogenous vegetable oil of oilseed Brassica according to the present invention in a low concentration of no more than 2 percent by weight based upon the total fatty acid content that is controlled by genetic means in combination with the other recited components as specified. In a preferred embodiment the erucic acid content is present in a concentration of less than 0.1 percent by weight and most preferably in a concentration less than 0.05 percent by weight based upon the total fatty acid content. The genetic means for the expression of such erucic acid trait can be derived from numerous commercially available canola varieties having good agronomic characteristics, such as BOUNTY, CYCLONE, DELTA, GARRISON, EMPACT, LEGACY, LEGEND, and PROFIT. Each of these varieties is registered in Canada and in commercially available in that country. Genetic means for the expression of such trait further can be obtained from FA677-39 (ATCC Assession No. 40409), FA677M5-132 (ATCC Assession No. 40523), Topas H6-90 (ATCC Assession No. 50524), F32-38-172-X (ATCC Assession No. 40624), and D-98-49-176 (ATCC Assession No. 40773). Also, genetic means for the expression of such low erucic trait can be obtained from 94SN-53574 (ATCC Assession No. 75813), 94SN-53662 (ATCC Assession No. 75814), and 94SN-52682 (ATCC Accession No. 75812) discussed hereafter. Such low erucic acid content offers a nutritional advantage.

Additionally, the endogenous vegetable oil of oilseed Brassica according to the present invention commonly includes a linoleic acid content of approximately 8 to 11. (e.g., approximately 9 to 10) percent by weight based upon the total fatty acid content. The linoleic acid component inherently exhibits more oxidative stability than the alpha-linolenic acid component. In a preferred embodiment the weight ratio of linoleic acid to alpha-linolenic acid in the endogenous oil is approximately 3:1 to 4:1.

In a preferred embodiment the Brassica oilseeds of the present invention further possess a glucosinolate content in the solid component following crushing and extraction of the oil component of less than 100 micromoles per gram, and most preferably less than 30 micromoles per gram. The glucosinolate content may be any one or a mixture of 3-butenyl glucosinolate, 4-pentenyl glucosinolate, 2-hydroxy-3-butenyl glucosinolate, and 2-hydroxy-4- pentenyl glucosinolate. The glucosinolate determination preferably is made on the air-dry-oil-free solid as measured by the gas liquid chromatograph method of the Canadian Grain Commission. The glucosinolate levels commonly are made possible by selecting starting materials which already are known to form the desired glucosinolate content, and by making selections which retain this value following combination with the recited traits.

If desired, a genetic means for tolerance to a herbicide when applied at a rate which is capable of destroying rape plants which lack said genetic means optionally may also be incorporated in the rape plants of the present invention as described in commonly assigned U.S. Pat. No. 5,387,758, that is herein incorporated by reference.

It has been found that the combination of desired traits described herein once established can be transferred into other plants within the same *Brassica napus, Brassica campestris,* or *Brassica juncea* species by conventional plant breeding techniques involving cross-pollination and selection of the progeny. It surprisingly has been demonstrated that the combination of characteristics is highly heritable, can be transmitted to progeny, and can be recovered in segregating progeny in subsequent generations following crossing. Also, once established the desired traits can be transferred between the *napus, campestris,* and *juncea* species using the same conventional plant breeding techniques involving pollen transfer and selection. Each of these species is recognized to include the same "A" genome as previously reported in the literature wherein the requisite genetic means can be located. The transfer of traits, such as low erucic acid content, between Brassica species, such as *napus* and *campestris,* by standard plant breeding techniques is already well documented in the technical literature. See, for instance, *Brassica Crops and Wild Allies Biology and Breeding,* edited by S. Tsunada, K. Hinata, and Gomex Campo, Japan Scientific Press, Tokyo (1980). As an example of the transfer of the desired traits described herein from *napus* to *campestris,* one may select a commercially available *campestris* variety such as REWARD, GOLDRUSH, and KLONDIKE, and carry out an interspecific cross with an appropriate plant derived from a *napus* breeding line, such as that discussed hereafter (i.e., 94SN-53662, 94SN-53574, or 94SN-52682). Alternatively, other *napus* breeding lines may be reliably and independently developed following mutagenesis. After the interspecific cross, members of the $F_1$ generation are self-pollinated to produce $F_2$ seed. Selection for the desired traits (e.g., unusually low saturated fatty acid content, etc.) is then conducted on single $F_2$ seeds which are then backcrossed with the *campestris* parent through the number of generations required to obtain a euploid (n=10) *campestris* line exhibiting the desired combination of traits wherein each trait is under genetic control and is expressed without cancellation as the result of the operation of the biochemical elongation and desaturation pathways necessary for the formation of the other recited traits.

In order to avoid inbreeding depression (e.g., loss of vigor and fertility) that may accompany the inbreeding of *Brassica campestris,* selected $BC_1$ plants that exhibit similar desired traits while under genetic control (e.g., elevated production of oleic acid, low saturated fatty acid production, and low alpha-linolenic acid production) advantageously can be sib-mated. The resulting seed from these crosses can be designated $BC_1SIB_1$ seed. Accordingly, the fixation of the desired alleles can be achieved in a manner analogous to self-pollination while simultaneously minimizing the fixation of other alleles that potentially exhibit a negative influence on vigor and fertility.

A representative *Brassica juncea* variety of low erucic acid content into which the desired traits can be similarly transferred include the commercially available ZEM variety. Also, low erucic acid *Brassica juncea* releases from Agriculture Canada, Saskatoon, Saskatchewan, Canada, such as the ZEHO variety, can be selected. *Brassica juncea* source materials of the lowest possible glucosinolate content preferably are utilized in order to eliminate the taste that is known to be characteristic of this component when present in the resulting endogenous vegetable oil.

The oilseed Brassica plants of the present invention preferably are provided as a substantially uniform stand of plants that are capable of forming oilseeds bearing an oil which exhibits the recited improved distribution of fatty acids. The Brassica oilseeds of the present invention preferably are provided as a substantially homogeneous assemblage of seeds which possess the improved distribution of fatty acids within the endogenous oil present therein. Also, the improved edible endogenous vegetable oil of the present invention preferably is provided in a quantity of at least one liter.

The improved oilseed Brassica plant of the present invention is capable of production in the field under conventional oilseed Brassica growing conditions that are commonly utilized during oilseed production on a commercial scale. Such oilseed Brassica exhibits satisfactory agronomic characteristics and is capable upon self-pollination of forming oilseeds that possess the improved distribution of fatty acids within the oil present therein. For the purposes of the present invention, "satisfactory agronomic characteristics" is defined as the ability to yield an oilseed harvest under standard field growing conditions of at least 85 percent, and preferably at least 90 percent, of the average yield for the three oilseed Brassica varieties of the same species most commonly grown on a commercial basis in the same region.

The ability to provide in a single edible endogenous vegetable oil the improved highly advantageous distribution of fatty acids of the present invention while under genetic control in the absence of the need for hydrogenation or other chemical or physical modification in spite of the readily apparent desirability to have such an improved rapeseed oil, is considered to be totally unexpected. An edible endogenous oil as presently claimed is novel and its production previously eluded all other researchers. It is particularly noteworthy that the improved overall combination of each of the recited fatty acid traits can be provided while under genetic control in the absence of cancellation as the result of the formation of other of the recited traits. One skilled in oilseed Brassica technology reasonably would have concluded that the operative elongation and desaturation biosynthetic pathways for fatty acid production would have conflicted with the simultaneous exhibition of the recited combination of traits, and would have precluded the simultaneous expression of all of the recited fatty acid characteristics in a single plant. In accordance with the concept of the present invention the recited traits surprisingly are combined in a single oilseed Brassica plant in the absence of antagonism among the recited traits. It further is surprising that the genetic means for the expression of the combination of the recited traits can be created via mutagenesis and satisfactorily combined in the absence of concomitantly expressing a deleterious significant modification in the production of non-seed lipids, such as those required in the formation of leaf membranes that are known to play an essential role in the support of photosynthesis and other important plant physiological functions. One skilled in the art would have reasonably anticipated that modifications in both storage lipids (TAG) and the non-storage lipids (primarily in the cell membrane) would take place. Modifications in non-storage lipids would be expected to significantly alter membrane function. Both the high oleic fatty acid and low alpha-linolenic fatty acid mutations are expected to reduce the proportion of polyunsaturated fatty acids in the membrane lipid fractions. If two such mutations were combined in a single plant, this would be expected to have a particularly deleterious effect on the membrane function. However, surprisingly no reduction in vigor, rate of growth, dry matter production, or seed yield has been observed in the plant material of the present invention that can be attributed to an impaired membrane function.

The improved edible endogenous vegetable oil of the present invention in a preferred embodiment exhibits a satisfactory flavor that can be described as being generally comparable to that of refined, bleached, and deodorized canola oil. The reduced saturated fatty acid content provides a significant nutritional benefit. Additionally, the enhanced thermal and oxidative stability of the endogenous oil provides in the absence hydrogenation or other chemical modification a highly attractive product that is well suited for a plurality of end uses. Representative usages include salad, frying, cooking, spraying, and viscous-food product applications. Handling and inventory considerations are greatly simplified since the endogenous vegetable oil of the present invention well fulfills the requirements for a wide variety of end uses and further possesses a more extended shelf life under ambient storage conditions. Each of these benefits is achieved in a straightforward manner in an endogenous product that inherently possesses superior health and nutrition properties.

The following Examples are presented as specific illustrations of the present invention. It should be understood, however, that the invention is not limited to the specific details set forth in the Examples.

EXAMPLE I

The procedure utilized in the creation of new plant material of the present invention designated 94SN-52682 is outlined in FIG. 1. Such procedure is described in greater detail hereafter.

A *Brassica napus* line designed D-98-49-176 derived from the GLACIER variety was selected as the source of the genetic means for low saturated fatty acid production. Seeds of this line are identified in commonly assigned U.S. Pat. No. 5,387,758, and are available from the American Type Culture Collection, 12301 Parklawn Drive, Rockville, Md. 20852, U.S.A., under Accession No. 40773.

For several generations the genetic means for low saturated fatty acid production was bulk crossed with elite *Brassica napus* lines. The low saturated fatty acid trait was thereby transferred to such elite *Brassica napus* lines possessing good agronomic characteristics by introgression. A resulting improved line designated 91SNQ-975 containing the genetic means for low saturated fatty acid production combined with good agronomic characteristics was selected.

A *Brassica napus* line designated FA677M5-132 derived from the REGENT variety was selected as the source of the genetic means for high oleic acid production. Seeds of this line are identified in commonly assigned U.S. patent application Ser. No. 287,708, filed Dec. 20, 1988, and are available from the American Type Culture Collection, 12301 Parklawn Drive, Rockville, Md. 20852, U.S.A. under Accession No. 40523.

For several generations the genetic means for high oleic acid production was bulk crossed with elite *Brassica napus* lines. The high oleic acid trait was thereby transferred to such elite lines by introgression. A resulting improved line designated 91SNQ-925 containing the genetic means for high oleic acid content combined with good agronomic characteristics was selected.

A cross was made between 91SNQ-975 and 91SNQ-925 whereby the genetic means for low saturated fatty acid content and high oleic acid content were successfully combined in a single plant designated 91SNQ-3249.

Plant 91SNQ-3249 was crossed with the BOUNTY variety of *Brassica napus* that possessed good agronomic characteristics. A progeny of this cross designated 92SNQ-292 was selected that continued to exhibit the genetic means for low saturated fatty acid content and high oleic acid content.

Plant 92SNQ-292 was crossed with the APOLLO variety of *Brassica napus* that possessed genetic means for low alpha-linolenic acid content. A heterozygous $F_1$ population designated 92SNQ-3717 was obtained. Plants of this $F_1$ population were self-pollinated to produce an $F_2$ population designated 93SN-6858 that segregated for each of the alleles or genetic means for the production of a low concentration saturated fatty acids, the production of a high concentration of oleic acid, and the production of a low concentration of alpha-linolenic acid. The $F_3$ seeds that formed on the $F_2$ plants following self-pollination were subjected to half-seed analysis to ascertain the fatty acid content of the endogenously produced vegetable oil present therein. An $F_3$ line designated 93SN-6927 was further evaluated for the successful integration of each of the alleles or genetic means for the production of a low concentration of saturated fatty acids, a high concentration of oleic acid, and a low concentration of alpha-linolenic acid.

$F_4$ seed designated 94SN-52682 was formed upon self-pollination of a single $F_3$ plant of the 93SN-6927 line. The $F_4$ seeds formed on this single $F_3$ plant following self-pollination were selectively harvested. An analysis of typical whole seeds of 94SN-52682 has determined that the following fatty acid distribution as reported in Table A is exhibited by the edible endogenous oilseed Brassica vegetable oil following simple crushing and extraction in the absence of hydrogenation or other chemical or physical modification:

TABLE A

| Fatty Acid | Number of Carbon Atoms Per Molecule | Number of Double Bonds Per Molecule | Weight Percent of Oil of 94SN-52682 |
|---|---|---|---|
| Lauric | 12 | 0 | non-detectable |
| Myristic | 14 | 0 | non-detectable |
| Palmitic | 16 | 0 | 2.38 |
| Palmitoleic | 16 | 1 | non-detectable |
| Stearic | 18 | 0 | 1.16 |
| Oleic | 18 | 1 | 83.04 |
| Linoleic | 18 | 2 | 9.25 |
| Alpha-linolenic | 18 | 3 | 2.49 |
| Arachidic | 20 | 0 | 0.39 |
| Eiconsenoic | 20 | 1 | 1.03 |
| Behenic | 22 | 0 | 0.18 |
| Erucic | 22 | 1 | non-detectable |
| Lignoceric | 24 | 0 | 0.07 |

It will be noted that the total saturated fatty acid content is 4.16 percent by weight based upon the total fatty acid content, and the saturated fatty acid content is 3.54 percent by weight based upon the sum of stearic and palmitic acids in relation to the total fatty acid content. Also, the weight ratio of linoleic acid to alpha-linolenic acid is 3.71:1.

Rapeseeds of the $F_4$ and $F_5$ generations designated 94SN-52682 have been deposited under the Budapest Treaty at the American Type Culture Collection, 12301 Parklawn Drive, Rockville, Md. 20852, U.S.A., and have received Accession No. 75812.

EXAMPLE II

The procedure utilized in the creation of new plant material of the present invention designated 94SN-53574 was identical to that utilized in connection with Example I with the exception that a different $F_4$ seed selection was made following the self-pollination of a different $F_3$ plant from the 93SN-6927 line.

An analysis of typical whole seeds of 94SN-53574 has determined that the following fatty acid distribution as reported in Table B is exhibited by the edible endogenous oilseed Brassica vegetable oil following simple crushing and extraction in the absence of hydrogenation or other chemical or physical modification:

TABLE B

| Fatty Acid | Number of Carbon Atoms Per Molecule | Number of Double Bonds Per Molecule | Weight Percent of Oil of 94SN-53574 |
|---|---|---|---|
| Lauric | 12 | 0 | non-detectable |
| Myristic | 14 | 0 | non-detectable |
| Palmitic | 16 | 0 | 2.02 |
| Palmitoleic | 16 | 1 | non-detectable |
| Stearic | 18 | 0 | 1.16 |
| Oleic | 18 | 1 | 82.63 |
| Linoleic | 18 | 2 | 9.08 |
| Alpha-linolenic | 18 | 3 | 2.81 |
| Arachidic | 20 | 0 | 0.52 |
| Eiconsenoic | 20 | 1 | 1.42 |
| Behenic | 22 | 0 | 0.22 |
| Erucic | 22 | 1 | 0.03 |
| Lignoceric | 24 | 0 | 0.13 |

It will be noted that the total saturated fatty acid content is 4.05 percent by weight based upon the total fatty acid content, and the saturated fatty acid content is 3.18 percent by weight based upon the sum of stearic and palmitic acids in relation to the total fatty acid content. Also, the weight ratio of linoleic acid to alpha-linolenic acid is 3.23:1.

Rapeseeds of the $F_4$ and $F_5$ generations designated 94SN-53574 have been deposited under the Budapest Treaty at the American Type Culture Collection, and have received Accession No. 75813.

EXAMPLE III

The procedure utilized in the creation of new plant material of the present invention designated 94SN-53662 was identical to that utilized in connection with Example I with the exception that a different $F_4$ seed selection was made following the self-pollination of yet another $F_3$ plant from the 93SN-6927 line.

An analysis of typical whole seeds of 94SN-53662 has determined that the following fatty acid distribution as reported in Table C is exhibited by the edible endogenous oilseed Brassica vegetable oil following simple crushing and extraction in the absence of hydrogenation or other chemical or physical modification:

TABLE C

| Fatty Acid | Number of Carbon Atoms Per Molecule | Number of Double Bonds Per Molecule | Weight Percent of Oil of 94SN-53662 |
|---|---|---|---|
| Lauric | 12 | 0 | non-detectable |
| Myristic | 14 | 0 | non-detectable |
| Palmitic | 16 | 0 | 2.36 |
| Palmitoleic | 16 | 1 | non-detectable |
| Stearic | 18 | 0 | 1.17 |
| Oleic | 18 | 1 | 81.30 |
| Linoleic | 18 | 2 | 10.54 |
| Alpha-linolenic | 18 | 3 | 2.86 |
| Arachidic | 20 | 0 | 0.42 |
| Eiconsenoic | 20 | 1 | 1.13 |
| Behenic | 22 | 0 | 0.18 |
| Erucic | 22 | 1 | non-detectable |
| Lignoceric | 24 | 0 | 0.04 |

It will be noted that the total saturated fatty acid content is 4.17 percent by weight based upon the total fatty acid content, and the saturated fatty acid content is 3.53 percent by weight based upon the sum of stearic and palmitic acids in relation to the total fatty acid content. Also, the weight ratio of linoleic acid to alpha-linolenic acid is 3.68:1.

Rapeseeds of the $F_4$ and $F_5$ generations designated 94SN-53662 have been deposited under the Budapest Treaty at the American Type Culture Collection, and have received Accession No. 75814.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An improved edible vegetable oil having an improved distribution of fatty acids formed by the process consisting essentially of crushing and extracting Brassica napus oilseeds wherein said distribution of fatty acids is endogenously formed and said vegetable oil exhibits (1) an alpha-linolenic acid content of 1 to less than 3.5 percent by weight based upon the total fatty acid content, (2) an oleic acid content of at least 77 up to approximately 84 percent by weight based upon the total fatty acid content, (3) a total saturated fatty acid content of no more than 4.5 percent by weight based upon the total fatty acid content, and (4) an erucic acid content of no more than 2 percent by weight based upon the total fatty acid content, and wherein each of said recited traits of said oil was controlled by genetic means in the absence of cancellation as the result of the formation of the other recited traits.

2. An improved edible vegetable oil according to claim 1 which exhibits an oleic acid content of at least 80 percent up to approximately 84 percent by weight based upon the total fatty acid content.

3. An improved edible vegetable oil according to claim 1 which exhibits a total saturated fatty acid content of 2.5 to 4.5 percent by weight based upon the total fatty acid content.

4. An improved edible vegetable oil according to claim 1 which exhibits a saturated fatty acid content of approximately 2 to 4 percent by weight based upon the sum of stearic and palmitic acids in relation to the total fatty acid content.

5. An improved edible vegetable oil according to claim 1 which exhibits a saturated fatty acid content of approximately 2 to 3.5 percent by weight based upon the sum of stearic and palmitic acids in relation to the total fatty acid content.

6. An improved edible vegetable oil according to claim 1 which exhibits a saturated fatty acid content of approximately 2.5 to 3.5 percent by weight based upon the sum of stearic and palmitic acids in relation to the total fatty acid content.

7. An improved edible vegetable oil according to claim 1 wherein said oil additionally exhibits a linoleic acid content of approximately 8 to 11 percent by weight based upon the total fatty acid content.

8. An improved edible vegetable oil according to claim 1 wherein said oil additionally comprises linoleic acid and exhibits a weight ratio of linoleic acid to alpha-linolenic acid of approximately 3:1 to 4:1.

9. An improved edible vegetable oil according to claim 1 which exhibits an erucic acid content of less than 0.1 percent by weight based upon the total fatty acid content.

10. An improved edible vegetable oil according to claim 1 which exhibits an erucic acid content of less than 0.05 percent by weight based upon the total fatty acid content.

11. An improved edible vegetable oil according to claim 1 wherein the genetic means for the expression of said recited traits (1), (2), and (3) are obtainable by mutagenesis.

12. An improved edible vegetable oil according to claim 1 wherein the genetic means for the expression of said recited traits (1), (2), and (3) are those present in 94SN-52682 having ATCC Accession No. 75812, 94SN-53574 having ATCC Accession No. 75813, or 94SN-53662 having ATCC Accession No. 75814.

13. An improved edible vegetable oil according to claim 1 wherein said oil is present in a quantity of at least one liter.

* * * * *